US009956195B2

(12) United States Patent
Venkatraman et al.

(10) Patent No.: US 9,956,195 B2
(45) Date of Patent: May 1, 2018

(54) STABLE LIPOSOMAL FORMULATIONS FOR OCULAR DRUG DELIVERY

(71) Applicants: Nanyang Technological University, Singapore (SG); Singapore Health Services Pte Ltd, Singapore (SG)

(72) Inventors: Subramanian Venkatraman, Singapore (SG); Jayaganesh V. Natarajan, Singapore (SG); Tina Howden, Singapore (SG); Freddy Boey, Singapore (SG)

(73) Assignees: Nanyang Technological University, Singapore (SG); Singapore Health Services Pte Ltd, Singapore (SG)

( * ) Notice: Subject to any disclaimer, the term of this patent is extended or adjusted under 35 U.S.C. 154(b) by 286 days.

(21) Appl. No.: 14/149,159

(22) Filed: Jan. 7, 2014

(65) Prior Publication Data

US 2015/0190359 A1    Jul. 9, 2015

(51) Int. Cl.
*A61K 9/127* (2006.01)
*A61K 31/5575* (2006.01)
*A61K 31/216* (2006.01)
*A61K 9/00* (2006.01)

(52) U.S. Cl.
CPC ......... *A61K 31/216* (2013.01); *A61K 9/0048* (2013.01); *A61K 9/127* (2013.01); *A61K 31/5575* (2013.01)

(58) Field of Classification Search
CPC .................................................... A61K 9/127
USPC ....................................................... 424/450
See application file for complete search history.

(56) References Cited

U.S. PATENT DOCUMENTS

| 4,938,965 | A |   | 7/1990  | Shek et al. |
|-----------|---|---|---------|-------------|
| 5,082,664 | A |   | 1/1992  | Lenk et al. |
| 5,120,870 | A |   | 6/1992  | Mizushima et al. |
| 5,478,819 | A |   | 12/1995 | Tarpila et al. |
| 5,925,375 | A |   | 7/1999  | Lenk et al. |
| 5,997,899 | A |   | 12/1999 | Ye et al. |
| 6,015,716 | A | * | 1/2000  | Harmon ............... G01N 33/579 424/283.1 |
| 6,486,208 | B1 |   | 11/2002 | Castillo et al. |
| 7,332,526 | B2 |   | 2/2008  | Bakhit et al. |
| 7,560,100 | B2 |   | 7/2009  | Pinchasi et al. |

(Continued)

FOREIGN PATENT DOCUMENTS

| WO | WO-1989003384 A1 | 4/1989 |
| WO | WO-1998043616 A1 | 10/1998 |

(Continued)

OTHER PUBLICATIONS

Al-Muhammad, J. et al., "Studies on the Formulation and In Virto Release of Ophthalmic Liposomes Containing Dexamethasone Sodium Phosphate," J Microencapsul, 1996, 13(2), pp. 123-130.

(Continued)

*Primary Examiner* — Gollamudi Kishore
(74) *Attorney, Agent, or Firm* — Cesari and McKenna, LLP

(57) ABSTRACT

A stable liposomal formulation for ocular delivery. The formulation contains a liposome that includes at least one lipid bilayer containing a phosphatidylcholine, and a prostaglandin $F_{2\alpha}$ encapsulated in the liposome. Also provided is a method for treating an ocular disorder with the formulation.

6 Claims, 3 Drawing Sheets

(56) References Cited

U.S. PATENT DOCUMENTS

| | | | |
|---|---|---|---|
| 7,592,325 B2 | 9/2009 | Jimenez et al. | |
| 8,293,789 B2 | 10/2012 | Jimenez-Bayardo et al. | |
| 8,409,606 B2 | 4/2013 | Sawhney et al. | |
| 8,470,784 B2 | 6/2013 | Liu et al. | |
| 8,771,745 B2 | 7/2014 | Robinson et al. | |
| 2001/0006648 A1 | 7/2001 | Yamauchi et al. | |
| 2003/0068365 A1 | 4/2003 | Suvanprakorn et al. | |
| 2003/0212001 A1 | 11/2003 | Peri et al. | |
| 2004/0137068 A1 | 7/2004 | Bhushan | |
| 2004/0224010 A1* | 11/2004 | Hofland | A61K 9/127 424/450 |
| 2004/0224011 A1 | 11/2004 | Rodrigueza et al. | |
| 2005/0054723 A1 | 3/2005 | Stjernschantz | |
| 2005/0220768 A1 | 10/2005 | McVey et al. | |
| 2005/0228048 A1 | 10/2005 | Asada et al. | |
| 2006/0165744 A1 | 7/2006 | Jamil et al. | |
| 2006/0188481 A1 | 8/2006 | Mori | |
| 2006/0211770 A1 | 9/2006 | Chang et al. | |
| 2006/0246145 A1* | 11/2006 | Chang | A61K 9/0051 424/490 |
| 2007/0026061 A1 | 2/2007 | Ali et al. | |
| 2007/0224255 A1 | 9/2007 | Moscoso Del Prado et al. | |
| 2007/0292496 A1 | 12/2007 | Vanrell et al. | |
| 2008/0021101 A1 | 1/2008 | Jimenez-Bayardo et al. | |
| 2008/0268020 A1 | 10/2008 | Philips et al. | |
| 2009/0234005 A1 | 9/2009 | Ishida et al. | |
| 2009/0280158 A1 | 11/2009 | Butuner | |
| 2009/0318549 A1 | 12/2009 | Butuner | |
| 2010/0112016 A1 | 5/2010 | Carli et al. | |
| 2010/0209477 A1 | 8/2010 | Butuner et al. | |
| 2010/0247606 A1 | 9/2010 | Robinson et al. | |
| 2010/0291226 A1 | 11/2010 | Mazzone et al. | |
| 2010/0310637 A1* | 12/2010 | Abdulrazik | A61K 38/28 424/450 |
| 2011/0008421 A1 | 1/2011 | Hara et al. | |
| 2011/0028477 A1 | 2/2011 | Aleo et al. | |
| 2011/0052493 A1* | 3/2011 | Fumero | C07K 14/47 424/9.1 |
| 2011/0070294 A1 | 3/2011 | Javeri et al. | |
| 2011/0152264 A1 | 6/2011 | Reunamaki et al. | |
| 2011/0294730 A1 | 12/2011 | Shantha et al. | |
| 2012/0184552 A1 | 7/2012 | Nakajima et al. | |
| 2012/0264681 A1 | 10/2012 | Braiman-Wiksman et al. | |
| 2012/0321719 A1 | 12/2012 | McDonnell et al. | |
| 2013/0053794 A1 | 2/2013 | Cadden et al. | |
| 2013/0216606 A1 | 8/2013 | Venkatraman et al. | |
| 2013/0273065 A1 | 10/2013 | Dana et al. | |
| 2013/0281454 A1 | 10/2013 | Schiffman et al. | |
| 2013/0309330 A1 | 11/2013 | Mastronardi | |
| 2014/0025022 A1 | 1/2014 | Cadden et al. | |
| 2014/0121612 A1 | 5/2014 | Rubin et al. | |
| 2014/0193347 A1 | 7/2014 | Thuresson et al. | |
| 2014/0213646 A1 | 7/2014 | Wong et al. | |

FOREIGN PATENT DOCUMENTS

| | | |
|---|---|---|
| WO | WO-2009051670 A3 | 4/2009 |
| WO | WO-2011053792 A2 | 5/2011 |
| WO | WO-2011/098578 A2 | 8/2011 |
| WO | WO-2012/021107 A2 | 2/2012 |
| WO | WO-2013164671 A1 | 11/2013 |
| WO | WO-2014039012 A1 | 3/2014 |
| WO | WO-2014153733 A1 | 10/2014 |

OTHER PUBLICATIONS

Bhardwaj, U. et al., "Physicochemical Properties of Extruded and Non-Extruded Liposomes Containing the Hydrophobic Drug Dexamethasone," Int. J Pharm., Mar. 2010, 388(1-2), pp. 181-189.

Sou, K., et al., "Bone Marrow-Targeted Liposomal Carriers: A Feasibility Study in Nonhuman Primates," Nanomedicine, Jan. 2010, 5(1), pp. 41-49.

Polozova et al "Formation of Homogeneous Unilamellar Liposomes from an Interdigitated Matrix" Biochimica et Biophysica Acta vol. 1668, pp. 117-125. 2005.

Davidson et al "Association and Release of Prostaglandin $E_1$ from Liposomes" Biochimica et Biophysica Acta vol. 1327, pp. 97-106. 1997.

\* cited by examiner

STABLE LIPOSOMAL FORMULATIONS FOR OCULAR DRUG DELIVERY

BACKGROUND

Intraocular pressure (IOP) in the eye is maintained by a continuous flow of aqueous humor produced by the ciliary body. Excess fluid flows out of the eye through the trabecular meshwork. If the outflow is blocked, aqueous humor builds up inside the eye leading to increased IOP and ocular hypertension. The ocular hypertension can damage the optic nerve, resulting in an optic neuropathy and irreversibly impaired vision. This condition, known as glaucoma, affects more than 60 million people worldwide and is the second leading cause of blindness. Increased IOP is the key modifiable risk factor for glaucoma.

Conventional treatments for ocular hypertensive and glaucoma patients include ocular surgery and topical eye drop instillation. These treatment modalities have drawbacks. For example, not all patients are candidates for ocular surgery. Additionally, although topical eye drops are generally considered to be effective, patients' long-term compliance with instillation schedules is a major issue. Ocular hypertension and glaucoma cannot be well controlled if patients do not adhere to the proper topical eye drop instillation schedule.

Topical eye drops contain drugs for controlling IOP which typically act by reducing fluid production by the eye, increasing fluid outflow, or by both mechanisms. Prostaglandin analogues, e.g., latanoprost, are potent drugs which can reduce IOP by increasing aqueous outflow through the uveoscleral pathway.

Typically, only 5% of free drug applied to the corneal epithelium via eye drops successfully penetrates through the cornea. As a result, the amount of drug reaching the aqueous humor often falls below the therapeutically effective concentration. This necessitates repeated administration. Additionally, a substantial portion of the drug can enter the circulation via the conjunctival sac, causing undesirable systemic side effects.

As an alternative to topical eye drops, subconjunctival injection of a sustained release IOP-reducing drug can be used to deliver drugs directly to the site of action. Such a delivery modality solves the problems of patient non-compliance with instillation schedules and inefficient drug transport across the cornea.

The need exists for a stable drug formulation for subconjunctival injection requiring a minimal frequency of administration for long-term stable control of IOP.

SUMMARY

To address the need for an improved treatment for intraocular pressure (IOP), a stable liposomal formulation for ocular delivery is provided. The formulation includes a liposome containing at least one lipid bilayer that includes a phosphatidylcholine. The formulation also contains a prostaglandin $F_{2\alpha}$ encapsulated in the liposome. Additionally, the liposome has a diameter of less than 2 µm.

Also provided is a method for treating an ocular disorder by administering the formulation described above.

The details of one or more embodiments of the invention are set forth in the drawings and description below. Other features, objects, and advantages of the invention will be apparent from the description and from the claims. All references cited herein are hereby incorporated by reference in their entirety.

BRIEF DESCRIPTION OF THE DRAWINGS

The description below refers to the accompanying drawings, of which.

DETAILED DESCRIPTION

Figure 1:
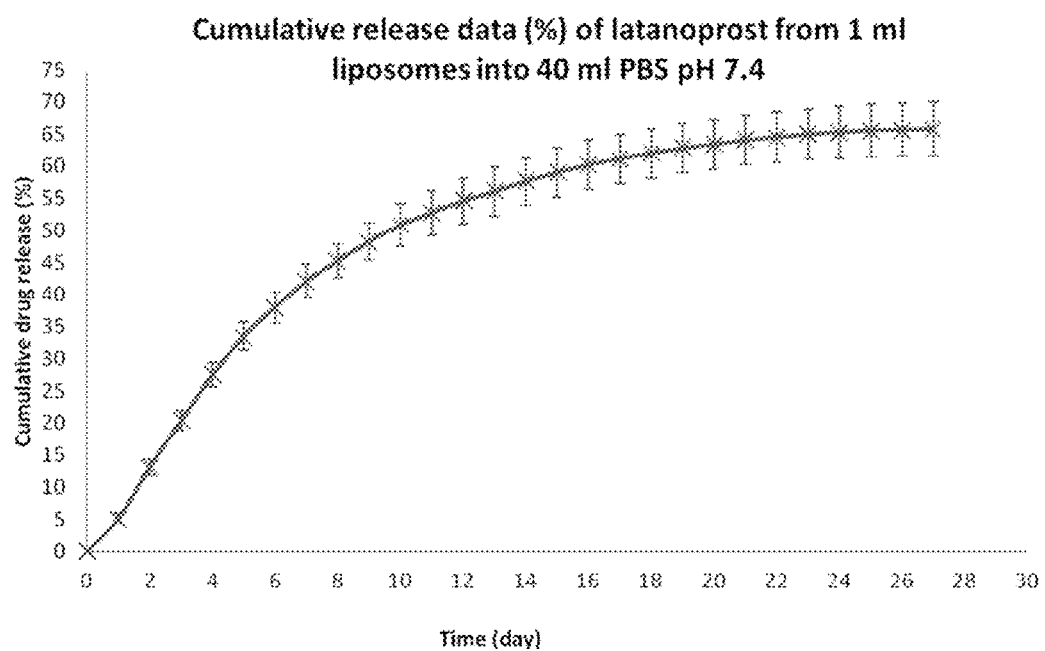
FIG. 1 is a plot of cumulative release of latanoprost from a palmitoyl oleoyl phosphatidyl choline (POPC) liposome versus time.

As mentioned above, a stable liposomal formulation for ocular delivery is provided. The formulation includes a liposome containing at least one lipid bilayer that includes a phosphatidylcholine. In an embodiment, the liposome is a unilamellar vesicle. In a preferred embodiment, the phosphatidyl choline is palmitoyl oleoyl phosphatidyl choline (POPC).

The formulation also contains a prostaglandin $F_{2\alpha}$ encapsulated in the liposome. The prostaglandin $F_{2\alpha}$ can be latanoprost, bimatoprost, travoprost, or carboprost. In a preferred embodiment, the prostaglandin $F_{2\alpha}$ is latanoprost.

The mole ratio of prostaglandin $F_{2\alpha}$ to POPC can be 0.01:1 to 0.5:1. In an embodiment, the mole ratio is 0.01:1 to 0.35:1. In a preferred embodiment, the stable liposomal formulation includes latanoprost and POPC at a mole ratio of 0.01:1 to 0.175:1. Additionally, the liposome can be formulated to include between 2 and 25 wt % of the prostaglandin $F_{2\alpha}$.

The liposome can have a diameter of less than 2 µm. In an embodiment, the diameter of the liposome is 100 nm to 300 nm, e.g., 100 nm, 150 nm, 200 nm, 250 nm, and 300 nm. In a preferred embodiment, the diameter is 100 nm. These nano-sized drug-loaded liposomes can release the prostaglandin $F_{2\alpha}$ slowly over time.

In an embodiment, the liposomal formulation described above can be a pre-constituted, ready-to-inject aqueous formulation for sub-conjunctival injection.

Also within the scope of the invention is a method for treating an ocular disorder that relies on administering the liposomal formulation described above. The ocular disorder can be ocular hypertension or glaucoma. Preferably, the disorder is glaucoma. In an embodiment, the liposomal formulation is administered by subconjunctival injection.

Administering the liposomal formulation described above can significantly reduce IOP at one hour post injection. More specifically, administering the liposomal formulation results in a reduction in IOP of at least 30% (e.g., 30%, 40%, and 50%) compared to the pretreatment IOP. Advantageously, the IOP remains reduced for as long as 4-6 months following a single injection.

As mentioned above, the injected liposomal formulation can slowly release the prostaglandin $F_{2\alpha}$, e.g., latanoprost, over several months. For example, 50% of the initial amount of drug in the liposomes can be released within 10 days after injection of the formulation into the eye. Preferably, 65% of the drug is released within 28 days of injection. Chronic topical application of anti-glaucoma drugs often induces ocular surface disease. The slow-release feature of the liposomal formulation obviates the need for daily applications of these drugs, thereby reducing or eliminating the concomitant side effects.

Typically, drugs which are not stable are lyophilized or frozen at a temperature of −20° C. or lower to prevent loss of activity over time. Notably, lyophilizing or freezing sustained release formulations of drug-loaded liposomes can adversely affect the drug release profile, resulting in an unpredictable variability in the drug effectiveness.

Advantageously, the liposomal formulation is stable for extended periods of time. For example, the formulation can be stored at 4° C. for up to 6 months (e.g., 1, 2, 3, 4, 5, and 6 months) without aggregation of the liposomes or loss of drug from them. Thus, the liposomal formulation can be stored in a vial at 4° C. for extended periods and then can be directly injected straight from the vial.

Without further elaboration, it is believed that one skilled in the art can, based on the description above, utilize the present invention to its fullest extent. The specific examples below are to be construed as merely illustrative, and not limitative of the remainder of the disclosure in any way whatsoever.

Example 1: Preparation of Large Unilamellar Vesicles (LUVs) for Drug Release Studies A thin film hydration technique was used to formulate latanoprost-loaded POPC liposomes for drug release studies. Briefly, POPC was weighed and dissolved in a chloroform: methanol (2:1 v/v) solvent mixture. Latanoprost (2 mg/ml stock solution in acetonitrile) was added to the lipid solvent mixture at a drug:lipid mole ratio of 0.175:1 and maintained at 40° C. The solvent mixture was added to a round bottomed flask in a rotary evaporator connected to a water bath maintained at 40° C. The flask was rotated at 100 rpm under low pressure for 1 h to remove the solvent, thereby forming a thin drug-loaded lipid film. Isotonic phosphate buffered saline (PBS; 150 mM, pH 5.5) was added to this film to form multilamellar vesicles (MLVs). The MLVs were extruded ten times through a polycarbonate filter (0.2 μm-0.08 μm). The extrusions resulted in the formation of LUVs having a size distribution of 0.09-0.12 μm in diameter.

Example 2: Preparation of LUVs for Drug Stability Studies

Drug-loaded LUVs were also prepared for stability studies. POPC was dissolved in PBS at a pH of 6.7 with constant stirring at room temperature for 2 h to form MLVs. The MLVs were extruded 3-5 times using three 80 nm sized polycarbonate membranes stacked together on a bench top extruder to form POPC LUVs. Latanoprost was dissolved in ethanol and the resulting solution, maintained in a round bottomed flask at 50° C. in a water bath, was dried under a stream of nitrogen gas to form a thin drug film. The drug film was hydrated with the POPC LUVs at room temperature for 2-3 h until no oil droplets were observed on the flask walls. A latanoprost:POPC mole ratio of 0.175:1 was used to prepare the drug-loaded LUVs. Latanoprost-loaded POPC LUVs were sterile filtered at room temperature using a 0.2 μm syringe filter and stored at 4° C. until analyzed. A similar method was used to prepare latanoprost-loaded egg PC liposomes.

Example 3: Characterization of Drug Loaded POPC Liposomes

Drug Release studies were performed by dialysing latanoprost-loaded POPC liposomes prepared as described in EXAMPLE 1 above against PBS at a pH of 7.4 and measuring by HPLC the amount of latanoprost released. The results are shown in FIG. 1. Over a 28 day period, approximately 65% of the latanoprost was released from the latanoprost-loaded POPC liposomes in a time-dependent manner.

The physical characteristics of the latanoprost-loaded POPC liposomes were determined essentially as described in Venkatraman et al., International Application Publication No. 2012/021107, the content of which is incorporated herein by reference in its entirety.

Figure 2A:
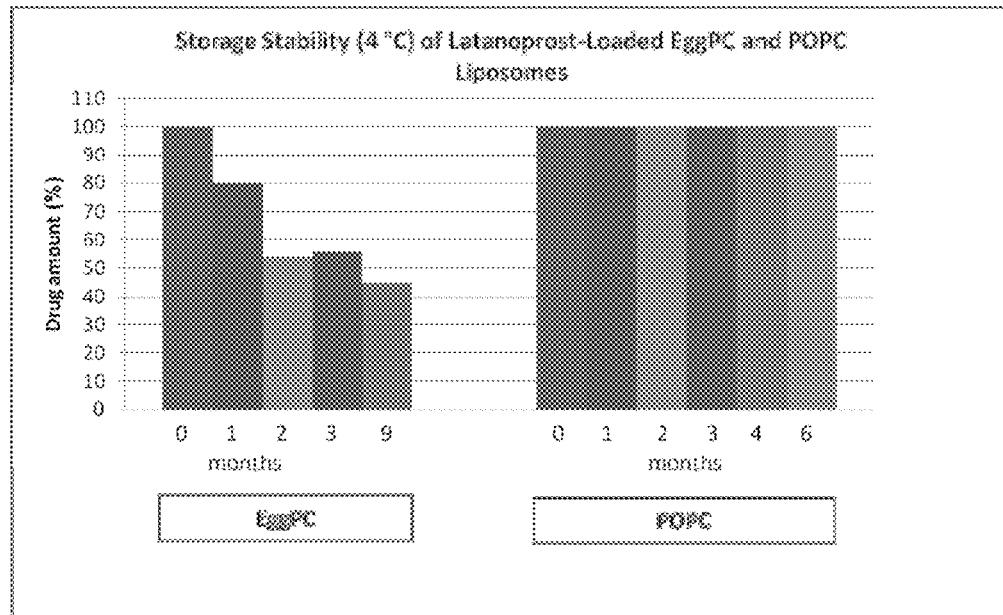
FIG. 2a is a plot of the percentage of the starting amount of latanoprost remaining in liposomes versus time for egg phosphatidyl choline (PC)-containing liposomes and POPC-containing liposomes.
Figure 2B:
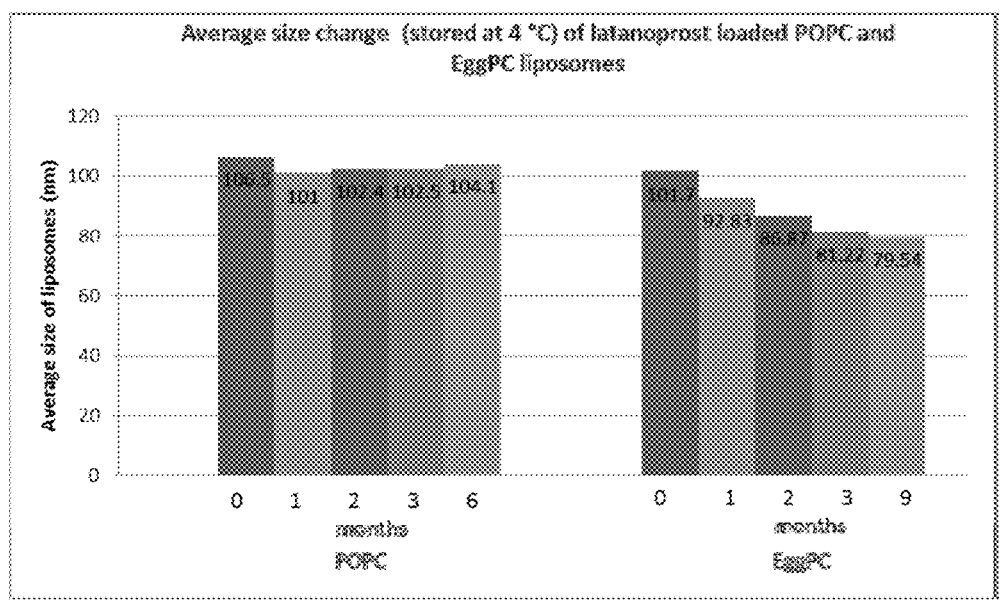
FIG. 2b is a plot of liposome size versus time of storage at 4° C.

The stability of latanoprost-loaded POPC liposomes prepared as described in EXAMPLE 2 above was measured and compared to similar latanoprost-loaded egg PC liposomes. Stability of the liposomes stored at 4° C. was assessed for a period of 6-9 months. Stability was assessed by measuring the average size of the liposomes as well as measuring by HPLC the concentration of latanoprost in the liposomes. The results are depicted in FIG. 2A and FIG. 2B. As shown in FIG. 2A, a significant amount of latanoprost was lost from egg PC liposomes over time, demonstrating a 45% reduction of the starting amount of latanoprost after 3 months of storage at 4° C. Unexpectedly, no measurable amount of latanoprost was lost from POPC liposomes even after 6 months of storage at 4° C. Turning to particle size, the results depicted in FIG. 2B reveal that the average size of latanoprost-loaded egg PC liposomes got progressively smaller over a 9 month period of storage at 4° C. Again unexpectedly, latanoprost-loaded POPC liposomes did not change measurably even after 6 months at 4° C. Notably, a change in size of a drug-loaded liposome will significantly alter the drug release kinetics.

Example 4: In Vivo Activity of Latanoprost Liposomal Formulation

The efficacy of the latanoprost liposomal formulation described above was tested in an animal model of glaucoma, namely, long tailed macaques (*Macaca fascicularis*) having ocular hypertension, defined as an IOP>18 mm Hg. Animal studies were performed in accordance with the statement for the use of animals in ophthalmic and vision research approved by the Association for Research in Vision and Ophthalmology. Additionally, the guidelines of the Animal Ethics Committee of the Singhealth Singapore Association for Assessment and Accreditation of Laboratory Animal Care were also followed.

The macaques were anesthetized by intramuscular injection of a mixture containing ketamine (5-10 mg/kg body weight) and acepromazine maleate (0.25 mg/kg body weight), together with a subcutaneous injection of atropine sulfate (0.125 mg/kg body weight). Their airway, respiration, and pulse were monitored during all procedures. One to two drops of 1% xylocaine was used as a topical anesthesia to reduce possible discomfort to the animals during subconjunctival injection. The animals' pupils were dilated with 2.5% phenylephrine hydrochloride and 1% tropicamide drops (Alcon Laboratories, French's Forest, NSW, Australia).

Latanoprost-loaded POPC liposomes were prepared by the technique described in EXAMPLE 2 above. A latanoprost liposomal formulation (100 μl) having an initial drug/lipid mole ratio of 0.175:1 was introduced by subconjunctival injection into both eyes of three animals. IOP was measured prior to injection and at daily and weekly intervals post-injection.

Figure 3:
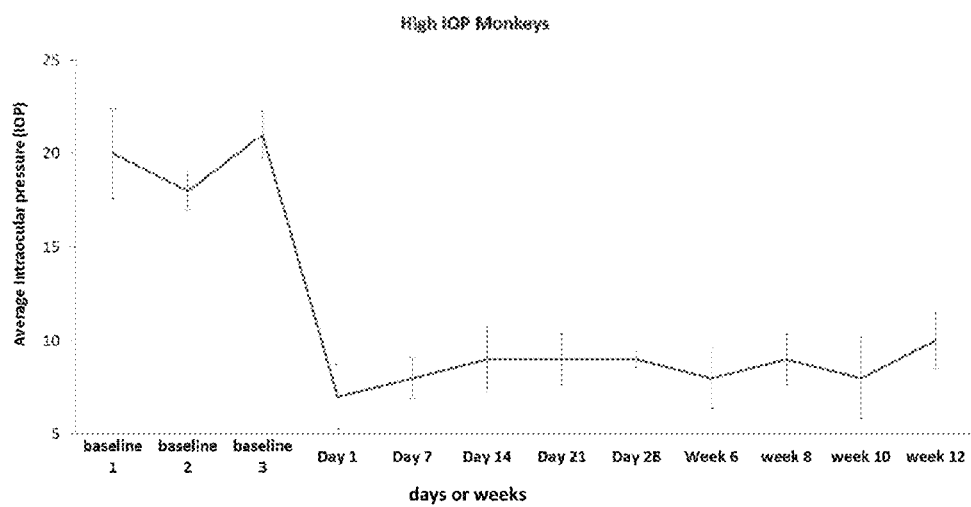
FIG. 3 is a plot of intraocular pressure versus days after a single subconjunctival injection of latanoprost encapsulated in a POPC-containing liposome

The monkeys were slightly anesthetized with ketamine (5 mg/kg body weight) before measurement of IOP. Again, 1-2 drops of 1% xylocaine was used as topical anesthesia to reduce possible discomfort to the animals involved during the measurement procedure. IOP was measured using a calibrated tonometer (Tono-Pen® XL, Reichert Technologies, Depew, N.Y.). IOP was monitored for three days pre-injection and for 120 days post-injection. The results are shown in FIG. 3. A single subconjunctival injection led to an initial rapid drop in intraocular pressure during the first day following the injection. The reduced IOP remained stable for at least 120 days post-injection.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A stable liposomal formulation for ocular delivery, the formulation comprising a liposome formed of palmitoyl oleoyl phosphatidyl choline (POPC), and latanoprost encapsulated in the liposome, wherein the liposome has a diameter of 100 nm to 300 nm, POPC is the sole lipid in the liposome, and the formulation is stable at 4° C. for up to 6 months.

2. The stable liposomal formulation of claim 1, wherein the formulation has a mole ratio of latanoprost to POPC of 0.01:1 to 0.5:1.

3. The stable liposomal formulation of claim 2, wherein the mole ratio of latanoprost to POPC is 0.01:1 to 0.175:1.

4. A method for treating ocular hypertension or glaucoma, the method comprising administering to an eye of a subject in need thereof the formulation of claim 1, wherein the formulation is administered via subconjunctival injection.

5. A method for treating ocular hypertension or glaucoma, the method comprising administering to an eye of a subject in need thereof the formulation of claim 2, wherein the formulation is administered via subconjunctival injection.

6. A method for treating ocular hypertension or glaucoma, the method comprising administering to an eye of a subject in need thereof the formulation of claim 3, wherein the formulation is administered via subconjunctival injection.

* * * * *